United States Patent [19]

Deem et al.

[11] Patent Number: 5,104,389
[45] Date of Patent: Apr. 14, 1992

[54] MEDICAL INSTRUMENT VALVE WITH FOAM PARTITION MEMBER HAVING VAPOR PERMEABLE SKIN

[75] Inventors: Mark E. Deem; Andrea T. Slater, both of Pembroke Pines, Fla.

[73] Assignee: Cordis Corporation, Miami Lakes, Fla.

[21] Appl. No.: 722,004

[22] Filed: Jun. 27, 1991

[51] Int. Cl.⁵ .............................................. A61M 5/00
[52] U.S. Cl. ...................................... 604/264; 604/167
[58] Field of Search ............... 604/167, 164, 158, 169, 604/172, 264, 265, 266; 251/368

[56] References Cited

U.S. PATENT DOCUMENTS

| | | | |
|---|---|---|---|
| 3,853,127 | 12/1974 | Spademan | 604/167 |
| 3,903,232 | 9/1975 | Wood et al. | |
| 4,000,739 | 1/1977 | Stevens | |
| 4,100,309 | 7/1978 | Micklus et al. | |
| 4,119,094 | 10/1978 | Micklus et al. | |
| 4,137,200 | 1/1979 | Wood et al. | |
| 4,610,665 | 9/1986 | Matsumoto et al. | |
| 4,626,245 | 12/1986 | Weinstein | |
| 4,642,267 | 2/1987 | Creasy et al. | |
| 4,769,013 | 9/1988 | Lorenz et al. | |
| 4,798,594 | 1/1989 | Hillstead | 604/167 |
| 4,813,966 | 3/1989 | Gilding et al. | |
| 4,906,240 | 3/1990 | Reed et al. | |
| 5,041,095 | 8/1991 | Littrell | 137/849 X |
| 5,041,100 | 8/1991 | Rowland et al. | |

OTHER PUBLICATIONS

Article by Michael Szycher-Periodical Entitled: Medical Design and Material, Feb. 1991, entitled Polyurethanes in Medical Devices-8 pages.

*Primary Examiner*—John J. Wilson
*Assistant Examiner*—Jeffrey A. Smith
*Attorney, Agent, or Firm*—Gerstman & Ellis, Ltd.

[57] ABSTRACT

A medical instrument such as a catheter introducer comprises a housing, with the housing carrying a valve for receiving and sealing an elongated member with penetrates the valve. The valve comprises an elastomeric partition member which, in turn, comprises a first, solid hydrophilic elastomer wall to limit the passage of aqueous liquids while permitting the passage of water vapor through the wall. The wall defines outer and inner faces, with the outer face carrying a hydratable lubricant material, and the inner face being bonded to a foamed elastomer material. The elastomer material facilitates sealing of the valve when an elongated member is penetrating therethrough, and it facilitates penetration of the elongated member. Also, the foamed elastomer material serves as a support for the hydrophilic elastomer wall, which is typically very thin to permit a high rate of water vapor diffusion.

20 Claims, 1 Drawing Sheet

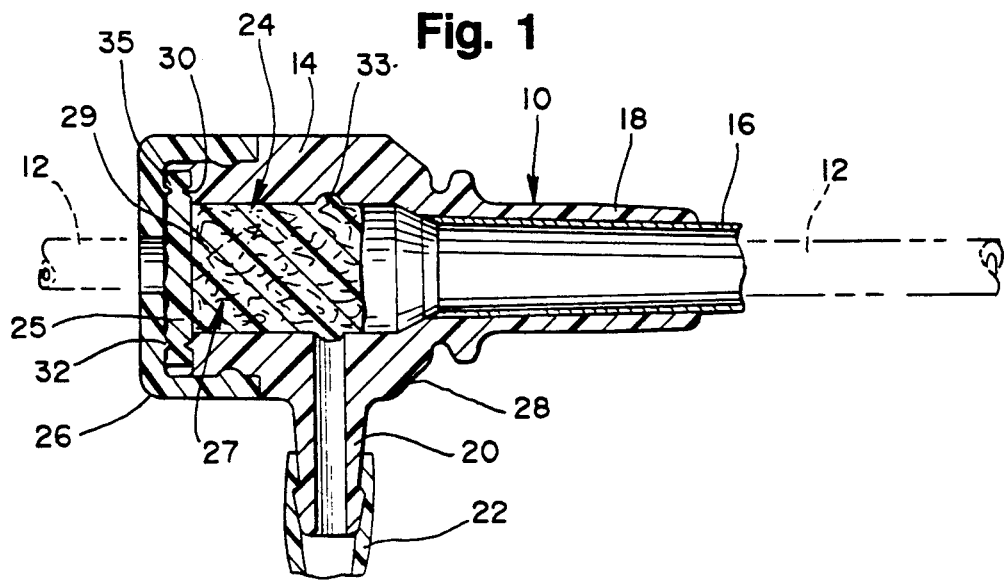
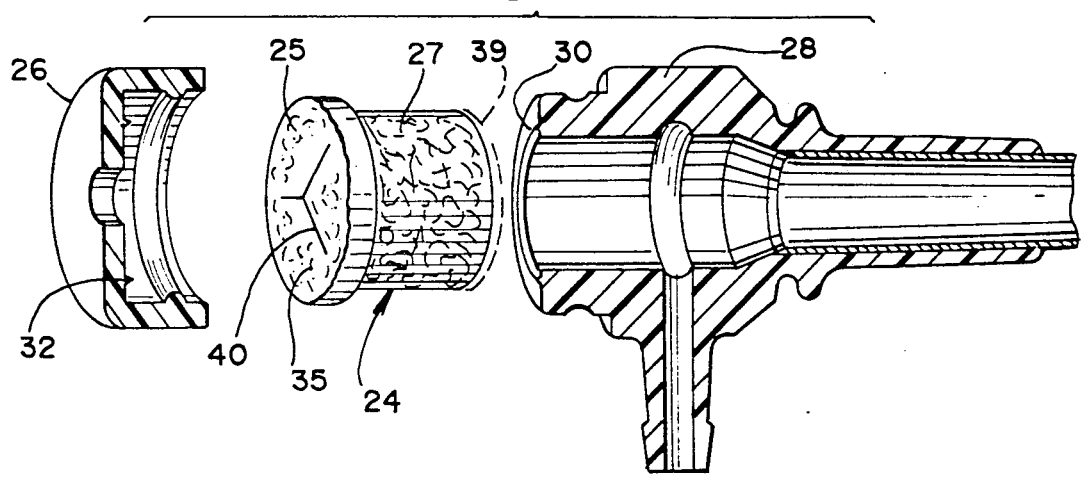
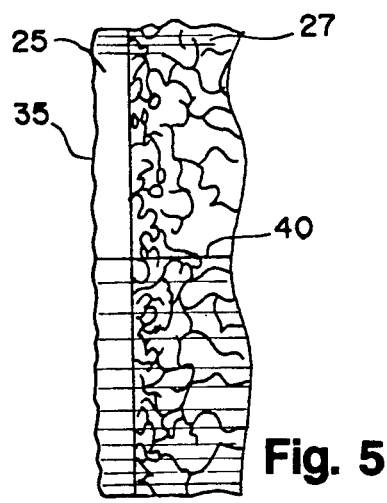

MEDICAL INSTRUMENT VALVE WITH FOAM PARTITION MEMBER HAVING VAPOR PERMEABLE SKIN

BACKGROUND OF THE INVENTION

Hemostasis valves are well-known, being currently used, for example, in arterial catheter introducers, used with catheters for performing percutaneous transluminal coronary angioplasty (PTCA), as well as catheters for angiographic procedures, for example where x-ray contrast fluid is inserted through a catheter into the coronary artery. The hemostasis valve is typically used to prevent the leakage of blood out of or around dilatation and other catheters which particularly enter into an artery, to prevent the reverse seepage of blood out of the patient into the operating field. Typically, hemostasis valves are conventionally positioned at the proximal ends of catheter introducers, which are used in conjunction with guidewires to facilitate the entrance of catheters into an artery or other blood vessel.

Numerous types of hemostasis valves are known. By way of example, see Stevens U.S. Pat. No. 4,000,739, Matsumoto et al. U.S. Pat. No. 4,610,655, Weinstein U.S. Pat. No. 4,626,245, and Hillstead U.S. Pat. No. 4,798,594.

In all of the previously cited patents, the hemostasis valves include an elastomeric partition of a solid, nonporous material which defines a slit through the partition, to facilitate the advancement of a catheter or guidewire through the hemostasis valve.

In the copending Kranys U.S. patent application No. 510,946, filed Apr. 19, 1990 and entitled Medical Instrument Valve Having Foam Partition Member, a hemostasis valve is disclosed for use with a catheter introducer or otherwise in which the elastomeric partition is a foamed elastomer. Such a material provides hemostasis, and may be used with a slit passing therethrough, or without a slit, since the foamed material is more easily penetrated by a guidewire or the like.

In the field of hemostasis valves such as those described above, it has been found to be desirable to place a hydrophilic lubricant material on the elastomeric partition of the hemostasis valve to facilitate the penetration of a catheter or guidewire therethrough. Particularly, hydratable hydrophilic materials are desirably used, such as the well-known hydrophilic lubricant sold under the brand name Hydromer. This material, and other hydrophilic lubricants, generally must be hydrated before they exhibit their desirable, slippery, lubricating characteristic. Typically, a separate hydration step is required by the addition of water to the lubricant, carried on the outer surface of the elastomeric partition member of hemostasis valves, followed often by a short waiting period, before the hydrophilic lubricant becomes sufficiently hydrated to exhibit its desirable lubricating characteristics.

Such hydrophilic lubricants tend to dry out after the hydration, so that the lubricity is again lost by the hemostasis valve, until another application of water is provided to rehydrate the material.

It would be desirable to provide a hemostasis valve which exhibits the good, slippery lubricity where the hydrophilic lubricant present remains hydrated for a long period of time, preferably during the entire procedure in which the hemostasis valve is involved, even if such a procedure might take hours or even days.

In accordance with this invention, a hemostasis valve is provided in which a hydratable lubricant material may be carried on the partition member, where the lubricant material can remain hydrated for an indefinitely long period of time during use, so that rehydration of the hydratable lubricant material ma not be required during use.

DESCRIPTION OF THE INVENTION

A medical instrument is provided, which instrument comprises a housing. The housing includes a valve for receiving and sealing an elongated member which penetrates the valve. This elongated member is, typically, a guidewire, generally followed by a catheter. The valve comprises an elastomeric partition member through which the elongated member can pass.

In accordance with this invention, the elastomeric partition member comprises a first, solid, hydrophilic elastomer wall, which limits the passage of aqueous liquids while permitting the passage of water vapor through the wall. The wall defines inner and outer faces, with the outer face carrying a hydratable lubricant material such as Hydromer or any similar hydrophilic lubricant coating. The inner face of the elastomer wall is bonded to a foamed elastomer material which is preferably generally hydrophilic in nature. The effect of this is that the valve provides good support for the elastomer wall, and sealing around an elongated member penetrating therethrough.

Typically, the solid, hydrophilic elastomer wall has a thickness ranging from about 0.0005 to 0.005 inch, with a typical thickness being about 0.001 inch, so that the passage of aqueous liquids is substantially prevented through the elastomer wall while water vapor readily passes therethrough, as well as through the foamed elastomer wall. Typically, both the hydrophilic elastomer wall and the foamed elastomer material are made of a hydrophilic polyurethane material, for example: Hypol, sold by W. R. Grace, and Co., Wood Patent Nos. 3,903,232 and 4,137,200 also disclose hydrophilic polyurethane foams.

If desired, the partition member may define a reclosable aperture such as a slit to further facilitate penetration of the elongated member through the partition member. The specific design of slit may be of any of the types disclosed in the patents cited above, so that the advantages of those particular slit designs may be combined with the advantage of the foamed elastomer partition member of this invention. Alternatively, the reclosable aperture may be a single, normally closed puncture hole through the partition member, which may be stretched and expanded by an advancing, elongated member to facilitate passage through the partition member.

Alternatively, the partition member of this invention may be aperture-free, with an aperture being formed through the partition by an advancing guidewire or other probe, to facilitate advancement of a subsequent catheter through the foamed partition member.

The foamed elastomer material of the partition member may be an open cell foam. Open cell foams are generally characterized by passages that interconnect most of the cells in the foam. Alternatively, open cell foams may be so open that they exhibit in a micrograph a fibrous, lacy aspect rather than appearing to define discrete cells with walls, and such structures are deemed to be one type of open cell foam for use herein. An advantage of open cell foams is that they tend to be more compliant than closed cell foams, since the air or other fluid in the cells can migrate to other cells as a probe passes through the partition member, stretching and expanding the member. Thus, the air is not compressed as in closed cell foams. In closed cell foams, the air in the cells has no way of escape, without breaking cell walls.

As a further advantage of open cell foams, they may contain desired lubricants, antithrombogenic agents, sterilizing agents, medicaments, or the like, which may pass onto the surface of the elongated member as it advances through the partition member. Thus, for example, an antithrombogenic agent such as heparin may be present in the foam.

For example, the foamed elastomer material may be impregnated with an antithrombogenic agent. Alternatively, the housing may define a side port which communicates laterally through the housing into intersecting relation with the partition member, to define a flow path for antithrombogenic agent to flow into the foamed elastomer material.

It is also preferred for the foamed elastomer material to define a cell size that increases in the direction extending away from the elastomer wall. Typically, the foamed elastomer material defines foam cells having diameters of substantially 0.1 to 200 microns for thin, sheet like partition members, or about 0.001 to 0.05 inch for thicker depth-type partition members as shown in the drawings. It is also often desirable for the partition member that includes the hydrophilic elastomer wall and the foamed elastomer material to define a depth that is greater than its maximum width.

The foamed elastomer material carries the first elastomer wall on one side thereof as discussed above. It is also preferred for a second, solid, hydrophilic elastomer wall to be bonded to the opposed side of the foamed elastomer material. The second wall preferably has a thickness of about 0.0005 to 0.005 inch, in the manner of the first elastomer wall, to also limit the passage of aqueous liquids while permitting the passage of water vapor through the second wall. The second wall may also carry a hydratable hydrophilic lubricant such as Hydromer or similar lubricant on its outer face.

Thus, particularly, blood is prevented from passage into the foamed elastomer material from the inner end of the hemostasis valve, except possibly for minor leakage through a slit or the like formed through the partition member. At the same time, when the first and second elastomer walls are thin, water vapor can pass therethrough. Thus, while the medical instrument such as a catheter introducer is implanted in the patient, water vapor migrating outwardly therethrough encounters the partition member and diffuses therethrough into contact with the hydratable lubricant material on the outer face of the first, solid, hydrophilic elastomer wall. Thus, the hydratable lubricant material is kept in a constant flow of diffused water vapor, while liquids are prevented from passage, so that the hydrated lubricant material retains its hydrated condition, and thus provides the desired, slippery lubrication without the need for a rehydration step by the addition of water or the like.

Specifically, the partition member used in the hemostasis valve of this invention may be made of Mitraflex, sold by PolyMedica Industries of Woburn, Mass., which is a material which up to the present time has been used primarily as a wound dressing and not as a partition member for a hemostasis valve. This material is made of polyurethane, having a solid, hydrophilic polyurethane skin about 0.001 inch thick, bonded to a foamed polyurethane layer in which the cells of the polyurethane are of increasing size as they are more remote from the solid polyurethane skin. This material, and other related materials, are described in the article by Michael Szycher in the periodical entitled Medical Design and Material, February, 1991, the article being entitled Polyurethanes in Medical Devices. Additionally, information about biocompatible materials which are porous but with an outer skin is disclosed in Gilding et al. U.S. Pat. No. 4,813,966 and Reed et al. U.S. Pat. No. 4,906,240.

Other hydratable lubricant materials besides the Hydromer material are as described in Micklus et al. U.S. Pat. Nos. 4,100,309 and 4,119,094, among other references. See also Creasy et al. U.S. Pat. No. 4,642,267 and Lorenz et al. U.S. Pat. No. 4,769,013.

Also, the allowed U.S. application of Stephen M. Rowland, Ser. No. 345,102, filed Apr. 28, 1989 and entitled Catheter and Hydrophilic, Friction Reducing Coating Thereon now U.S. Pat. No. 5,041,100 discloses another system for providing a hydratable lubricating surface on a plastic article.

DESCRIPTION OF DRAWINGS

In the drawings,

FIG. 1 is a longitudinal sectional view of a hemostasis valve in accordance with this invention, carried on a catheter introducer;

FIG. 2 is an exploded perspective view of the hemostasis valve of FIG. 1, with some parts shown in section;

FIG. 3 is a proximal end view of the partition member shown in FIGS. 1 and 2;

FIG. 4 is a distal end view of the partition member shown in FIGS. 1 and 2; and

FIG. 5 is a highly magnified, fragmentary sectional view of the partition member of this invention, taken along line 5—5 of FIG. 3.

DESCRIPTION OF SPECIFIC EMBODIMENTS

Referring to the drawings, FIGS. 1 and 2 show the proximal end of a catheter sheath introducer 10 which may be of entirely similar design to any of various known, commercially available catheter sheath introducers, except as otherwise described herein. Catheter sheath introducer 10 is adapted to receive an inner catheter 12 as shown for insertion into the vascular system of a patient. Catheter sheath introducer 10 is used to introduce the catheter into a blood vessel, while preventing blood backflow along the outside surface of the catheter during procedures in which the catheter is inserted into the vessel.

Catheter sheath introducer 10 defines outer tubular housing 14, which carries cannula portion 16 (mostly broken away) of the catheter sheath introducer 10, positioned in attached, telescoping relation with tubular protrusion 18 of the housing. Side port 20 may be of conventional design, being adapted for telescoping connection with plastic tubing 22.

Housing 14 also carries a self-sealing, penetrable barrier as elastomeric partition member 24. In accordance with this invention, elastomeric partition member 24 comprises a first, solid, hydrophilic elastomer wall 25, which is typically made of solid polyurethane and has a thickness of about 0.001 inch (the drawing showing a structure of greater thickness for purposes of illustration). Elastomer wall 25 is bonded to a foamed elastomer material 27, both materials 25 and 27 being preferably of hydrophilic polyurethane, being bonded together by appropriate heat sealing or any other desired means. The foamed polyurethane portion 27 may be substantially thicker than elastomer wall 25, being particularly shown in FIG. 1 to extend down to the level of side port 20 so that side port 20 directly communicates with the foamed elastomer portion 27. In fact, the depth of partition member 24 may exceed its maximum width, as shown in FIG. 1. Also, the individual cells of the foamed elastomer portion 27 are shown to be of a graduated size, being smaller in area 29 adjacent to elastomer wall 25, and growing in size to a maximum size at the opposed end 31 of foamed elastomer portion 27.

Accordingly, it becomes possible to soak the hydrophilic, foamed elastomer portion 27 with an antithrombogenic agent such as heparin solution, administered through side port 20. Annular passage 33 is provided to cause the heparin solution to distribute entirely around the foamed portion 27, from where the heparin solution can migrate throughout the foamed portion.

Specifically, the cell sizes of the foamed portion may range from 0.001 to 0.05 inch, with the latter value approximating the size of the cells in area 31 and the former value approximating the size of the cells in area 29. However, if the Mitraflex material or the like is being used, it is much thinner than the partition member 24 shown so that the entire partition member would occupy the area shown in FIG. 1 to be occupied by hydrophilic elastomer wall 25. Also, such a material may define smaller foam cells having diameters of substantially 0.1 to 200 microns.

Partition member 24 may be preimpregnated with an antithrombogenic agent so that the agent is not necessarily added through side port 20, and side port 20 may be used for its customary purpose in a catheter introducer. Also, since the foamed area 27 is hydrophilic, even in the embodiment shown in FIG. 1 the side port 20 may be used in the conventional manner of a catheter introducer to provide saline flush or the like since the saline will pass out of partition member 24 with ease, since the invention typically utilizes an open cell foam.

Elastomer wall 25 carries a layer of hydratable lubricant material 35 on its outer surface, for example the Hydromer material as described above.

Housing 14 may comprise casing portions 26, 28 which are sealed together in snap-fit, telescoping relation, and which peripherally capture partition 24, or elastomer wall 25, between them as shown. Alternatively, casing 26 may be a screw cap, for adjustable, compressive retention of the periphery of partition 24 or wall 25. Annular ribs 30, 32 may be provided in each casing portion to provide more positive capture of partition 24 or wall 25. Additionally or alternatively, partition 24 may be solvent, heat, or ultrasonically bonded to one or both of casing portions 26, 28.

As shown in FIG. 2, partition 24 may define a Y-shaped slit 40, or any other design of slit as may be desired, extending therethrough to facilitate the penetration of a catheter or guidewire through partition 24. As taught in Hillstead U.S. Pat. No. 4,798,594, slit 40 may rotate in helical manner as it extends through partition 24 for improved sealing characteristics.

Alternatively, partition 24 may be used without any slit. Rather, one may press a guidewire or other probe through the partition 24, forming a slit that exactly fits the transverse dimensions of the probe.

FIGS. 3 and 4 show opposed sides of partition member 24, but FIG. 4 shows an embodiment where slit 40 does not extend all the way through partition member 24. Basically, the slit may be used to start penetration of an elongated member, but the elongated member may be capable of penetrating through the foamed material 27 without use of a slit.

By this invention, when a catheter introducer is implanted into the vascular system of a patient and a catheter 12 is inserted, typically following a guidewire, it is desirable to maintain the hydration of hydratable lubricant coating 35 after initially hydrating it at the beginning of the procedure by wetting it with sterile saline or the like. In accordance with this invention, water passing through the lumen of catheter introducer tube 16, and outside of catheter 12, freely migrates through the open cell foam 27, along with liquids such as blood which may migrate through the foamed section. However, blood or the liquids will not pass through elastomer wall 25. Also, liquids typically will not migrate in any significant quantity through slit 40, which may be designed to prevent the back migration of blood whether or not a catheter or a guidewire is present or absent therein.

However, water vapor migrating through foam 27 is also capable of migrating by diffusion through elastomer wall 25. As it does so, it enters into contact with the hydratable lubricant material 35, thus replacing moisture that is lost by evaporation from the hydratable lubricant material 35. Accordingly, during the procedure, even if it is long or the patient carries the hemostasis valve for a matter of hours or days, a constant flow of water vapor through elastomer wall 25 will replenish lost water from hydratable layer 35, so that the layer retains its hydration, and is immediately available to provide lubricity for the insertion of a catheter or a guidewire on short notice without the need to rehydrate layer 35.

As an alternative mode, referring to FIG. 2, it is possible to add to partition member 24 a second elastomer wall 39, shown in dotted lines as being bonded to the face of foamed elastomer material 2 that is opposed to the face that carries first elastomer wall 25.

Thus, blood coming back between catheter 12 and catheter introducer tube 16 is prevented by elastomer wall 39 from entering into foam portion 27. However, when elastomer wall 39 is made of a solid, hydrophilic polyurethane material which is approximately 0.001 inch in thickness, in a manner similar to first elastomer wall 25, water vapor is still free to migrate through the thickness of partition member 24 to provide hydrating action to hydratable lubricant layer 35.

The above has been offered for illustrative purposes only, and is not intended to limit the scope of the invention of this application, which is as defined in the claims below.

That which is claimed is:

1. A medical instrument comprising a housing, said housing including a valve for receiving and sealing an elongated member which penetrates said valve, said valve comprising an elastomeric partition member, the improvement comprising, in combination:

said partition member comprising a first, solid, hydrophilic elastomer wall to limit the passage of aqueous liquids while permitting the passage of water vapor through said wall, said wall defining outer and inner faces, said outer face carrying a hydratable lubricant material, said inner face being bonded to a first side of a foamed elastomer material, to facilitate penetration of said elongated member therethrough and sealing of said valve.

2. The medical instrument of claim 1 in which said partition member defines a reclosable slit extending therethrough to further facilitate penetration of the elongated member.

3. The medical instrument of claim 1 in which said partition member is slit-free.

4. The medical instrument of claim 1 in which said foamed elastomer material is an open cell foam.

5. The medical instrument of claim 4 in which said foamed elastomer material defines a cell size that increases in the direction extending away from said elastomer wall.

6. The medical instrument of claim 4 in which said foamed elastomer material defines foam cells having diameters of substantially 0.1 to 200 microns.

7. The medical instrument of claim 1 in which said elastomer wall and said foamed elastomer material are made of polyurethane.

8. The medical instrument of claim 1 in which said foamed elastomer material is hydrophilic in nature.

9. The medical instrument of claim 1 in which said partition member defines a depth that is greater than the maximum width of said partition member.

10. The medical instrument of claim 1 in which said foamed elastomer material is impregnated with an antithrombogenic agent.

11. The medical instrument of claim 1 in which said housing defines a side port communicating laterally through said housing into intersecting relation with said partition member, to define a flow path for antithrombogenic agent to flow into said foamed elastomer material.

12. The medical instrument of claim 1 in which said first elastomer wall has a thickness of no more than about 0.005 inch.

13. The medical instrument of claim 12 in which said foamed elastomer material defines a second side opposite to said first side of said foamed elastomer material and a second solid, hydrophilic elastomer wall bonded to said second side of said foamed elastomer material, said second wall having a thickness of no more than about 0.005 inch to limit the passage of aqueous liquids while permitting the passage of water vapor through said second wall.

14. The medical instrument of claim 13 in which said first and second solid elastomer walls each have a thickness of at least 0.0005 inch.

15. A medical instrument comprising a housing, said housing including a valve for receiving and sealing an elongated member which penetrates said valve, said valve comprising an elastomeric partition member, the improvement comprising, in combination:

said partition member comprising a first, solid, hydrophilic elastomer wall having a thickness of no more than about 0.005 inch to limit the passage of aqueous liquids while permitting the passage of water vapor through said wall, said wall defining outer and inner faces, said outer face carrying a hydratable lubricant material, said inner face being bonded to a first side of an open cell foam, hydrophilic elastomer material, to facilitate penetration of said elongated member therethrough and sealing of said valve while permitting the migration of water vapor through said partition member.

16. The medical instrument of claim 15 in which said partition member defines a reclosable slit extending therethrough to further facilitate penetration of the elongated member.

17. The medical instrument of claim 15 which defines a cell size that increases in the direction extending away from said elastomer wall.

18. The medical instrument of claim 15 in which said elastomer wall and foamed elastomer are made of polyurethane.

19. The medical instrument of claim 15 in which said foamed elastomer material is impregnated with an antithrombogenic agent.

20. The medical instrument of claim 15 in which said foamed elastomer material defines a second side opposite said first side of said foamed elastomer material and a second, solid, hydrophilic elastomer wall bonded to said second side of said foamed elastomer material, said second wall having thickness of no more than about 0.005 inch to limit the passage of a aqueous liquids while permitting the passage of water vapor through said second wall.

* * * * *